United States Patent
Criss

(10) Patent No.: US 9,248,044 B2
(45) Date of Patent: Feb. 2, 2016

(54) UNDERGARMENT FOR POST-SURGICAL MASTECTOMY PATIENTS

(71) Applicant: JEAN CRISS MEDIA LLC, Summit, NJ (US)

(72) Inventor: Jean Criss, New Providence, NJ (US)

(73) Assignee: JEAN CRISS MEDIA LLC, Summit, NJ (US)

( * ) Notice: Subject to any disclaimer, the term of this patent is extended or adjusted under 35 U.S.C. 154(b) by 293 days.

(21) Appl. No.: 13/952,124

(22) Filed: Jul. 26, 2013

(65) Prior Publication Data

US 2014/0031775 A1    Jan. 30, 2014

Related U.S. Application Data

(60) Provisional application No. 61/676,237, filed on Jul. 26, 2012.

(51) Int. Cl.
| | |
|---|---|
| A61F 5/44 | (2006.01) |
| A61F 5/03 | (2006.01) |
| A41C 3/00 | (2006.01) |
| A41D 13/12 | (2006.01) |
| A61F 13/14 | (2006.01) |

(52) U.S. Cl.
CPC ............. *A61F 5/4408* (2013.01); *A41C 3/0064* (2013.01); *A41D 13/1245* (2013.01); *A61F 5/03* (2013.01); *A41B 2400/32* (2013.01); *A61F 13/145* (2013.01); *A61F 13/148* (2013.01)

(58) Field of Classification Search
CPC ....... A41C 3/00; A41C 3/0064; A41C 3/0028; A41C 3/005; A41C 3/02; A41C 3/148
USPC ................... 450/36, 39, 58, 89, 1; 2/114, 104
See application file for complete search history.

(56) References Cited

U.S. PATENT DOCUMENTS

| | | | |
|---|---|---|---|
| 3,837,006 A * | 9/1974 | Laseman | 2/89 |
| 5,158,541 A | 10/1992 | McCurley | |
| 5,496,205 A | 3/1996 | Lee | |
| 5,560,043 A * | 10/1996 | Armstrong | 2/69.5 |
| 5,782,670 A | 7/1998 | Whisman | |
| 5,815,833 A * | 10/1998 | Kuo | 2/69.5 |
| 6,061,831 A * | 5/2000 | Rudolph et al. | 2/69.5 |
| 6,263,509 B1 * | 7/2001 | Bowen | 2/69 |
| 6,390,885 B1 | 5/2002 | Brooks | |
| 6,604,248 B1 * | 8/2003 | Brown | 2/456 |
| 7,810,170 B1 * | 10/2010 | Guthrie | 2/69.5 |
| 8,405,058 B2 * | 3/2013 | Slinkard et al. | 250/516.1 |
| 2006/0173427 A1 | 8/2006 | Urbina et al. | |

(Continued)

OTHER PUBLICATIONS

"*Jodee Post-Surgery, Leisure, Sleep Bras & Camisoles*" http://espanol.makemeheal.com/mmh/product/mastectomy/jodee/index.vm?procid=33&catid=767.

(Continued)

*Primary Examiner* — Gloria Hale
(74) *Attorney, Agent, or Firm* — Leason Ellis LLP

(57) ABSTRACT

An undergarment is provided in the form of a brassiere which includes comfort and stylistic features to assist in post-surgical recovery. In other implementations, a camisole is provided which includes comfort and stylistic features to assist in post-surgical recovery. In one application, the post-surgical undergarment is configured to assist in the recovery of mastectomy patients.

23 Claims, 14 Drawing Sheets

(56) References Cited

U.S. PATENT DOCUMENTS

| | | | |
|---|---|---|---|
| 2007/0061965 A1* | 3/2007 | Crawford | 5/413 R |
| 2008/0066229 A1* | 3/2008 | Auer et al. | 5/482 |
| 2008/0209609 A1* | 9/2008 | Panek | 2/66 |
| 2008/0235848 A1* | 10/2008 | Wilder et al. | 2/69.5 |
| 2009/0036023 A1 | 2/2009 | Bertini | |
| 2012/0311763 A1* | 12/2012 | King | 2/69.5 |

OTHER PUBLICATIONS

"The Woman's Personal Health Resource, Inc." *Mastectomy Bras, Breast Forms, and More at Womans Personal Health.* Women's Personal Health Resource, Inc., 2009. Web. http://www.womanspersonalhealth.com.

"Back at Home and It . . . " *Wearing My BRCA Genes.* The Coraline Theme., Apr. 12, 2011. Web. http://youngbrca1.wordpress.com/tag/surgeon/.

* cited by examiner

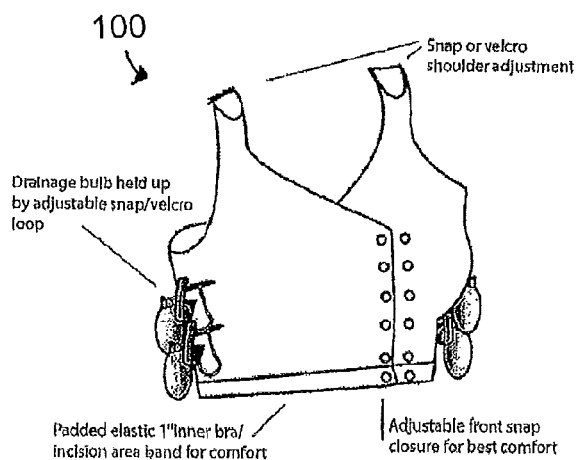
FIG. 1
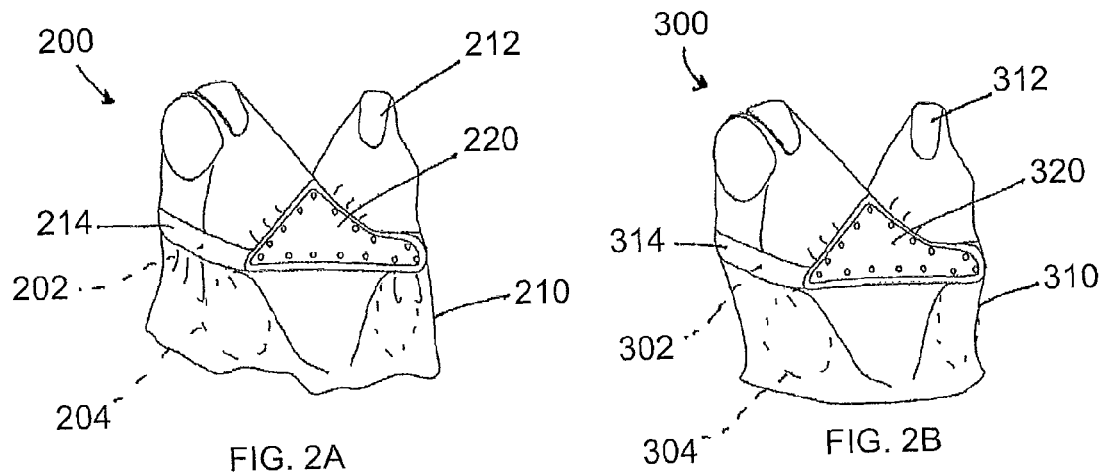
FIG. 2A
FIG. 2B

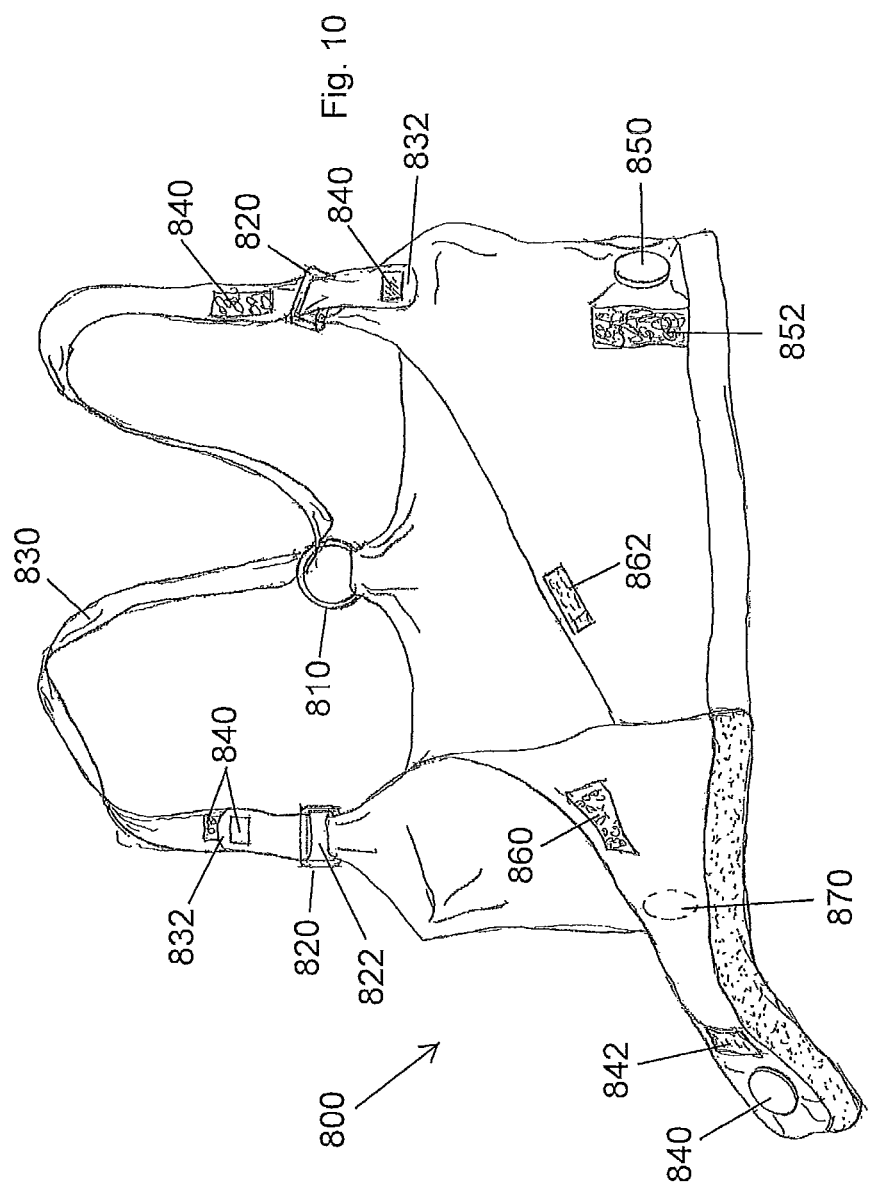

UNDERGARMENT FOR POST-SURGICAL MASTECTOMY PATIENTS

CROSS REFERENCE TO RELATED APPLICATION

The present application claims the benefit of U.S. patent application Ser. No. 61/676,237, filed Jul. 26, 2012, which is hereby incorporated by reference in its entirety.

BACKGROUND

The present invention relates generally to various undergarments and other clothing for patients who have undergone mastectomies to assist in the recovery process. In particular, the present invention relates to multi-purpose undergarments and related products for post-operative recovery of mastectomy procedures to provide versatility and comfort with functionality for the necessary tubing and drainage required for these patients.

Following a mastectomy procedure, the patient may experience pain, discomfort, limited mobility, and self-consciousness. The patient may further require prolonged self care of the surgical site to prevent infection and promote proper healing.

Currently available technologies include brassieres and camisoles which provide compression to reduce and/or prevent swelling at the surgical site. These technologies further include slits or holes though which drainage tubes are passed to assist in draining fluids from the surgical site. The drainage tubes are attached to drainage bulbs or bags which are positioned external to the brassiere or camisole and which collect the fluids for subsequent disposal. These bulbs are commonly pinned to the exterior of the brassiere or camisole and may come loose and pull on the skin or incision site of the drainage tube as the bulbs fill with fluid. Further, these bulbs and drainage tubes are unsightly and may further contribute to the patient's feelings of self-consciousness, depression, and/or post-traumatic stress.

Currently available technologies require that the patient move or position their body into uncomfortable positions to place and remove the brassiere onto their body. Currently available technologies further lack sufficient adjustability whereby the brassiere or camisole is capable of being adjusted to accommodate the physical requirements of the patient.

Thus, while options exist for assisting a patient in post-surgical recovery from a mastectomy procedure, challenges still exist. Accordingly, it would be an improvement in the art to augment or even replace current techniques with newer enhancements and techniques.

SUMMARY

The systems and methods of the present disclosure have been developed in response to problems, and needs in the art that have not yet been fully resolved by currently available systems and methods. Thus, the systems and methods herein provide a solution to current challenges within the art.

In some implementations of the present invention a brassiere is provided which includes comfort and stylistic features to assist in post-surgical recovery. In other implementations, a camisole is provided which includes comfort and stylistic features to assist in post-surgical recovery.

BRIEF DESCRIPTION OF THE DRAWING FIGURES

In order that the manner in which the above-recited and other features and advantages of the invention are obtained will be readily understood, a more particular description of the invention, briefly described above, will be rendered by reference to specific embodiments thereof, which are illustrated in the appended drawings. These drawings depict only typical embodiments of the invention and are not therefore to be considered to limit the scope of the invention.

FIG. 1 is a perspective view of a post-surgical brassiere in accordance with a representative embodiment of the present invention;

FIGS. 2A and 2B are perspective views of a post-surgical camisole in accordance with the present invention;

FIG. 10 is front perspective view of a post-surgical brasserie according to another embodiment in a partially open condition;

DETAILED DESCRIPTION OF CERTAIN EMBODIMENTS

Figure 3A:
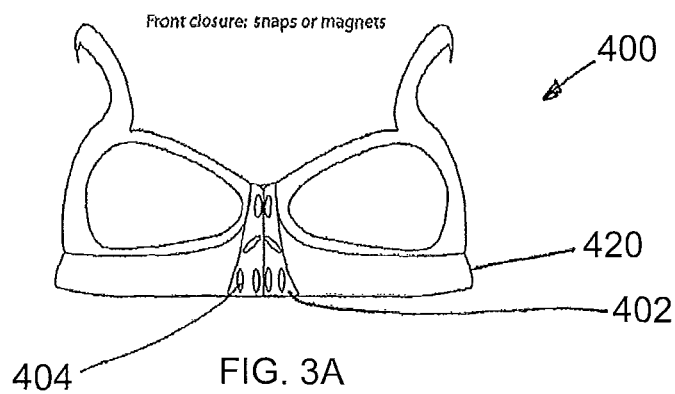
FIGS. 3A and 3B are elevation views of a post-surgical brassiere in accordance with a representative embodiment of the present invention.

Embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

As used herein, the term "undergarment" may include any clothing item that is designed to assist in post-surgical recovery of a mastectomy patient, namely, a brassiere, a camisole, a bathing suit, a vest, a shirt, a bandeau, a sports bra, shapewear, a girdle, a tank top, a wrap, a bandage, a sweatshirt, a hoodie, a towel, a coat, and lingerie. In general, one having skill in the art will appreciate that the teachings of the present invention may be applied to any piece of clothing or other material compatible with the underlying methodologies and principles disclosed herein.

Referring now to FIG. 1, a post-surgical brassiere 100 is shown. Various embodiments of post-surgical brassiere 100 include one or more of the following features: (1) fastener closure (e.g., hook and loop material) at the shoulder; (2) adjustable shoulder straps to provide adjustability for patient size and height; (3) adjustable loops (e.g., hook and loop material) or elastic fasteners to hold drainage bulbs and tubes; (4) side insert slits to accommodate insertion of empty drainage bulb following the surgical procedure; (5) shortened drainage tubes to hold drainage bulb closer to the patient's body thereby limiting exposure of the bulbs through the patient's clothing; also results in drainage bulbs being held close to the patient's body thereby preventing pulling on the insertion site; (6) multiple rows of front closures for comfort and adjustability once the postsurgical gauze padding is removed; (7) a padded elastic band that is positioned under the patient's breasts for comfort; may include a viscoelastic polyurethane foam that shapes to the physical features of the patient; and (8) a decorative print and/or pattern to improve the patient's feelings of selfconsciousness. It will be appreciated that the foregoing features are merely exemplary and not limiting of the present invention and in addition, two or more of any of the foregoing features can be combined in one embodiment.

Referring now to FIG. 2A, a post-surgical camisole 200 is shown. Post-surgical camisole 200 is configured to hold and conceal the drainage tubes 202 and bulbs 204 behind the skirt 210. As such, tubes 202 and bulbs 204 are hidden. Various embodiments of post-surgical camisole 200 further include one or more of the following features: (1) long line adjustable shoulder straps 212 formed of hook and loop material for full support and adjustability; (2) elastic inset 214 under breast incision for support; and (3) cross over support panel 220 with a closure or fastener selected from snaps, magnets, hook and loop material, buttons, or hook and eye or any other type of mechanical fastener.

Referring now to FIG. 2B, a post-surgical camisole 300 is shown. Post-surgical camisole 300 may include each of the features taught in accordance with post-surgical camisole 200. Additionally, post-surgical camisole 300 includes a fitted skirt 310 that provides support and comfort in addition to covering or concealing the drainage bulbs 304 and tubes 302.

Figure 3B:
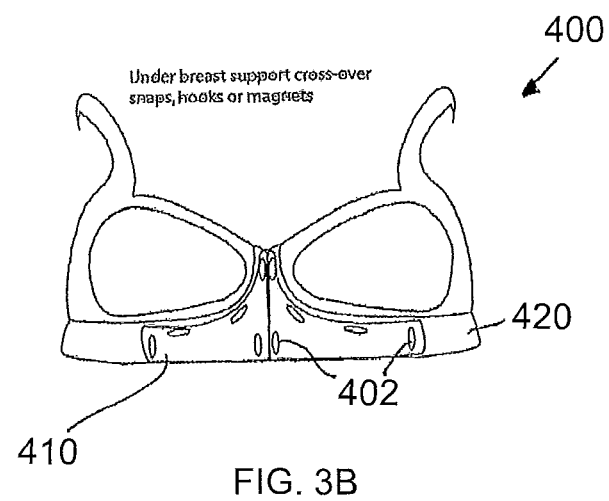

Referring now to FIGS. 3A and 3B, a post-surgical brassiere 400 is shown. In some embodiments, post-surgical brassiere 400 comprises a form of a sports bra that includes a front closure 402 which includes a plurality of magnets 404. The magnets 404 are positioned on opposing surfaces of brassiere 400 such that the front of the brassiere 400 is closed by joining the opposing magnets 404.

In other embodiments, post-surgical brassiere 400 comprises a cross-over closure 410 which includes a plurality of magnets 404, as shown in FIG. 3B. The magnets 404 are positioned on opposing surfaces of brassiere 400 such that the brassiere 400 is closed by wrapping the cross-over closure 410 under the patient's breasts such that the opposing magnets 402 are joined. Post-surgical brassiere 400 may further include a padded elastic under-band 420 having a height of approximately 1 inch to approximately 2 inches. Under-band 420 may include any material, and preferably may include a viscoelastic polyurethane foam that shapes to the physical features of the patient.

Figure 4:
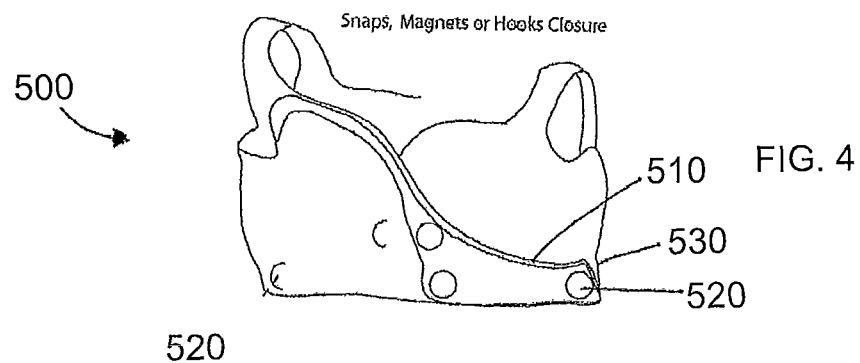
FIG. 4 is a perspective view of a post-surgical brassiere in accordance with a representative embodiment of the present invention.

Referring now to FIG. 4, a post-surgical sports bra 500 is shown. Sports bra 500 may include a cross-over front closure 510 having a minimal number of snaps or magnets 520. Sports bra 500 may further include a comfort under-band 530 having similar features and characteristics as those previously discussed herein.

Figure 5:
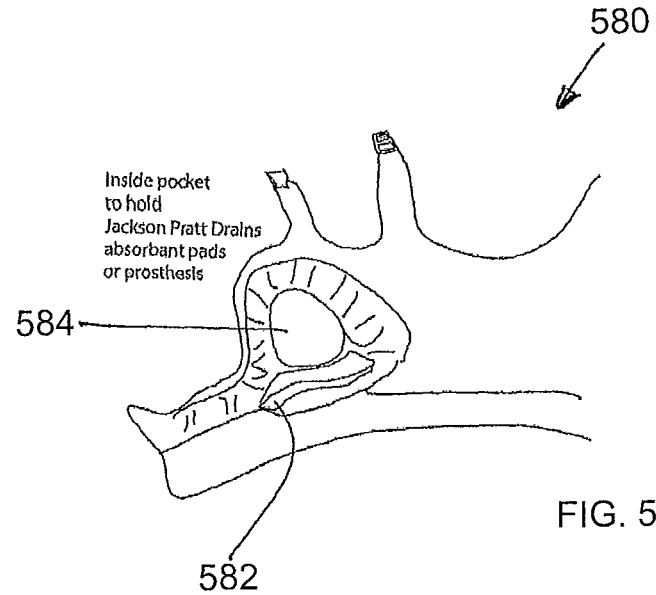
FIG. 5 is a perspective view of post-surgical brassiere having an interior pocket for holding drainage tubes and an absorbent pad in accordance with a representative embodiment of the present invention.
Figure 9:
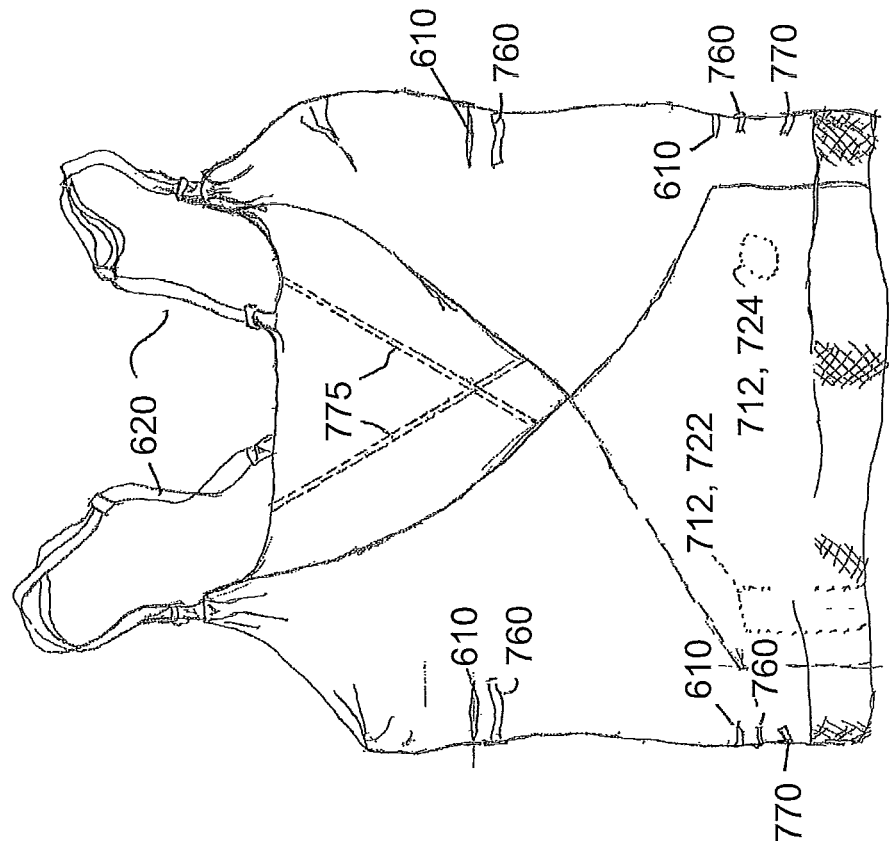
FIG. 9 is a front elevation view showing the post-surgical brasserie in the assembled condition.

Referring now to FIG. 5, an inside view of a post-surgical camisole 580 is shown. In some embodiments, camisole 580 comprises a pocket 582 that is located or positioned in the cup 584 of the camisole 580. Pocket 582 may include a solid or mesh material. In some instances, pocket 582 is configured to hold a drainage bulb and tube. In other embodiments, pocket 582 is configured to hold an absorbent pad that received fluid either directly from the surgical site or from a drainage tube inserted into the surgical site. For example, an absorbent pad may include a feminine hygiene pad or a nursing pad. The pad may include a color indicator to signal when the pad needs to be changed. Some embodiments provide a pad that includes a wicking material, or another technology whereby suction or negative pressure within the pad draws fluid from the patient's surgical site. Accordingly, the pad may replace the use of a drainage bulb. The pad may further reduce the overall visibility of the surgical site, as compared to the generally bulky nature of drainage bulbs.

In accordance with the spirit of the present invention, the teachings disclosed herein can be implemented in any number of different garments that are constructed for wearing by a patient. For example, various types and forms of other potential undergarments or garments are shown that may be modified for use in post-surgical recovery of mastectomy patients. In some instances, a vest is provided as a recovery garment for male patients. In other instances, a bandeau is provided as a recover garment for mastectomy patients. Tops and shirts may also be provided as recovery garments for mastectomy patients.

The undergarments and garments of the present invention may include any type or style of fabric or combinations of fabrics. For example, in some embodiments a post-surgical undergarment is provided that is comprised of a stretch fabric, such as Celliant®. In other embodiments, a post-surgical undergarment is provided that is comprised of Holofiber®.

The undergarments and garments of the present invention may further include features for enhancing recovery by optimizing energy patterns within the patient's body. For example, in some embodiments a post-surgical undergarment is provided which includes biomagnets. The biomagnets may be incorporated into the garment as a type of enclosure or fastener. Alternatively, the biomagnets may be incorporated in the garment solely as a therapeutic element.

The undergarments and garments of the present invention may further include features and technologies to provide antimicrobial properties and/or odor absorptions protection to enhance hygiene. For example, in some embodiments a post-surgical undergarment is provided which incorporates LIFE® products, fabrics, coatings, and/or materials.

Now referring to FIGS. 6-9, a post-surgical undergarment 600 is shown. The undergarment 600 is in the form of a sport bra; however, it will be appreciated that the construction and feature described below can be implemented into other types of undergarments. The undergarment 600 incorporates the CRISSCROSS® construction described herein and thus, the undergarment 600 is adjustable so as to accommodate different sized patients and to provide a level of comfort that other post-surgical garments lack. The CRISSCROSS® construction results from crisscrossing overlapping fabric layers that are attached to one another at strategic points as described herein.

Figure 11:
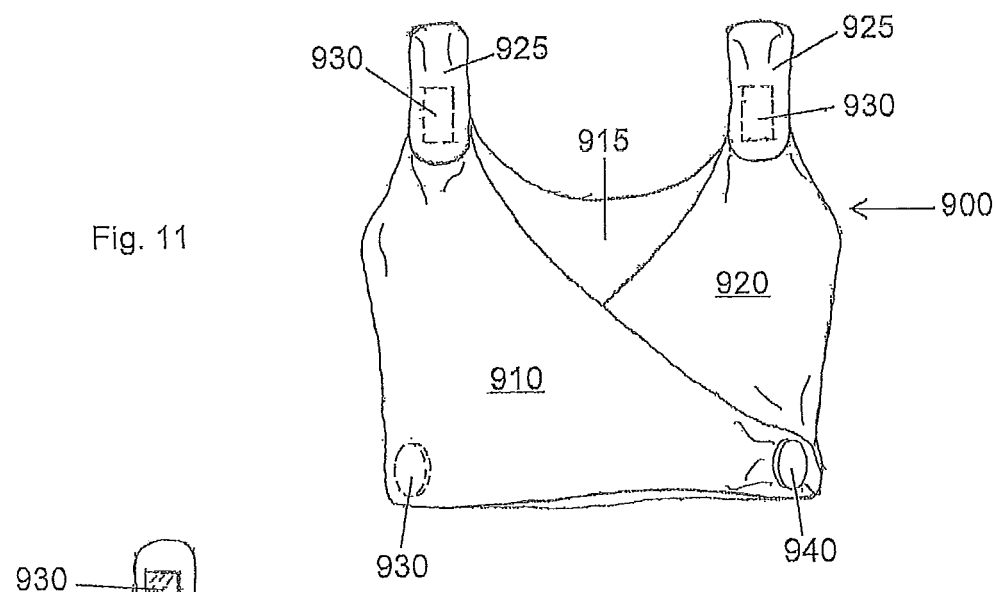
FIG. 11 is front elevation view of a garment according to another embodiment.
Figure 12:
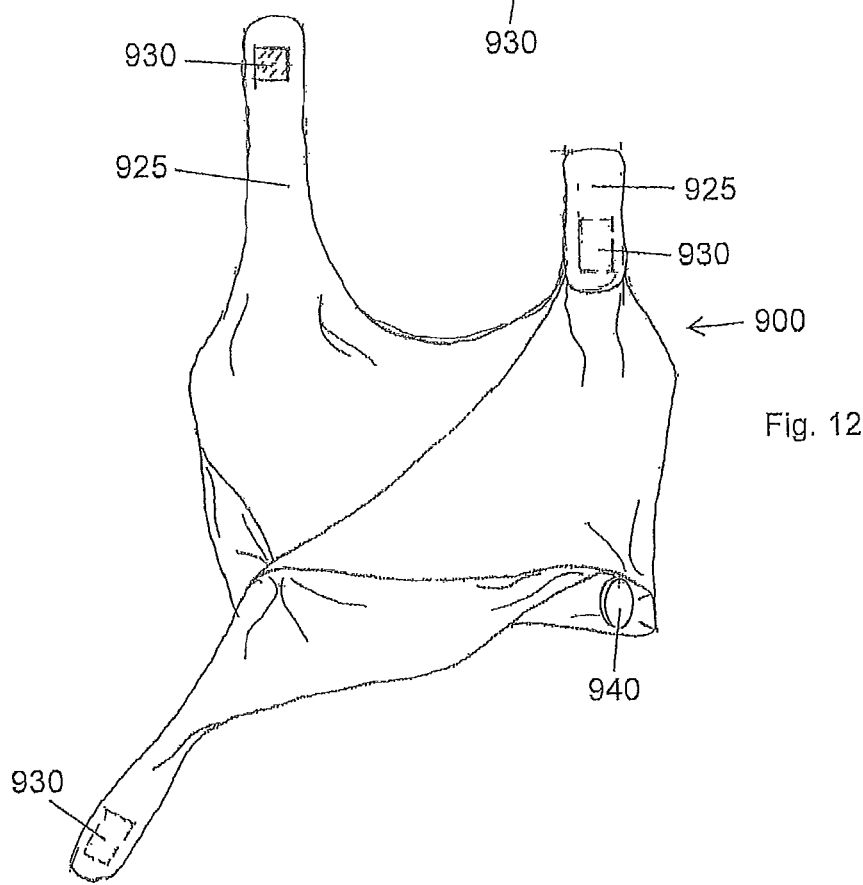
FIG. 12 is front perspective view of the garment in a partially open condition.

The undergarment 600 has a main body section 605 that is disposed about the breast area and torso of the patient and a pair of shoulder straps 620 that are attached to the main body section 605 to provide support and hold the undergarment in place. Typically, the main body section 605 and the straps 620 can be formed of the same material or can be formed of a different material. The straps 620 can be elastic in nature to provide optimal fit and to allow easy elongation thereof and thus, the straps 620 are adjustable in nature to accommodate different sized patients and provide optimal fit. In other designs, as shown in FIGS. 11 and 12, the straps 620 can be adjustable using fasteners.

In accordance with the present invention, the main body section 605 can be fully opened to allow placement around the body of the patient and subsequent wrapping of the main body section 605 around the patient to secure the undergarment around the patient's body. The main body section 605 thus has a front 612 and a back 614 and in the fully opened position shown in FIGS. 7 and 8, the main body section 605 is defined by a center section 630, a first wrap section 640, and a second wrap section 650, with the center section 630 disposed between the two wrap section 640, 650. In one embodiment, each wrap section 640, 650 can be thought of as extending outwardly beyond the respective shoulder strap to a free end. As described herein, the wrap sections are sequentially wrapped around the front of the patient in a CRISSCROSS® manner to attach the garment about the patient.

The first wrap section 640 is defined by a first edge 642 (free end) and the second wrap section 650 is defined by a second edge 652 (free end). In the illustrated embodiment, the edges 642, 652 are vertical edges that are substantially parallel to one another in the fully opened position. However, it will be understood that the edges 642, 652 are not limited to being vertical edged parallel to one another and can readily take other forms.

It will be appreciated that the undergarment 600 can come in different traditional sizes and in such case, the size (cut) of the main body section and/or wrap sections can vary depending upon the overall size (e.g., an XL garment will have larger overall dimensions).

In the illustration embodiment, bottom edges of the first and second wrap sections 640, 650 are straight cuts, while top edges of the first and second wrap sections 640, 650 can be contoured, such as being curved or angled (as shown), etc. As described below, when the wrap sections 640, 650 are closed (wrap) about the patient's body during normal wear, the top edges of the overlapping wrap sections 640, 650 define the neckline of the undergarment. The neckline can be a scoop neck, crew neck, V-neck, or any other type of neckline suitable for the intended application.

In accordance with the present invention, the undergarment has a fastening mechanism 700 that allows the undergarment 600 to be worn with increased comfort and fit as a result of the improved adjustability and overall support provided by the undergarment 600 without sacrificing the desired functionality of the undergarment as described herein. The fastening mechanism 700 can incorporate one or more types of strategically placed fastening elements to allow the first and second wrap sections 640, 650 to be wrapped around the patient's body and then secured in a desired position (location) so as to complete the undergarment and fully surround the patient's body.

In the illustrated embodiment, the fastening mechanism comprises a set of first fasteners associated with one wrap section and a set of second fasteners associated with the other wrap section. The set of first and second fasteners in part is used to attach the second edge 652 to an interior section of the first wrap section 640 and the set of first and second fasteners are used to attach the first edge 642 to the exterior surface of the second wrap section 650. For example, one fastener 712 of the first set is located at or near the first edge 642, while the other fastener 714 of the set 710 is spaced therefrom and located along an inner surface of the first wrap section 640 spaced from the edge 642. The fasteners 712, 714 allow the second wrap section 650 to be attached to the inner face (surface) of the first wrap section 640. Similarly, the second set of fasteners includes one fastener 722 that is located at or near the second edge 652, while the other fastener 724 of the set 720 is located along an exterior surface of the second wrap section 650 spaced from the edge 652 thereof.

As described herein, the garment is attached around the user (patient) in an adjustable manner by attaching the two wrap sections to one another across the front of the patient (which represents the surgical site).

However, it will be appreciated that the garment can be constructed to have the opposite construction in that the first wrap section can be attached to the inner surface (face) of the second wrap section. The second wrap section is thus the section that is folded over across the exterior surface (face) of the first wrap section.

The selection and dimensions and placement of the individual fasteners provide the desired CRISSCROSS® construction and provide not only improved comfort but also improved versatility and accommodation as a result of the ability to fully open the undergarment and to attach the wrap sections 640, 650 in an at least partially overlapping manner (CRISSCROSS® manner).

In one embodiment, the fasteners 714, 722 are in the form of sections of hook and loop material. For example, the fasteners 714, 722 can each be in the form of one or more strips, patches, pads, etc. of hook and loop material. When multiple parts are used for each fastener 714, 722, the individual parts are purposely positioned to permit the desired attachment between the second edge (end) 652 and the inner or interior surface (face) of the first wrap section 640. As shown, the fasteners 714, 722 can be in the form of a single strip of hook and loop material.

The fasteners 712, 724 which serve to complete the wrap and attachment process so as to provide an undergarment that extends and is secured around the body of the patient. In one embodiment, the fasteners 712, 724 are in the form of one or more permanent magnets or the like. For example, each fastener 712, 724 can be in the form of a series of permanent magnets or alternatively, each fastener can be a single permanent magnet.

To securely attach the undergarment to a patient according to one embodiment, the second wrap section 650 is wrapped across the patient's front (across the breast and stomach area) and is positioned in a desired position that is comfortable to the user. The first wrap section 640 is then wrapped across the patient over the exterior of the second wrap section 650 and the first end (end) 642 of the first wrap section 640 is attached to the exterior surface of the second wrap section 650 using fasteners 712, 724. As discussed herein, the material of the undergarment preferably has a degree of elasticity to allow the wrap sections 640, 650 to be stretched to achieve a secure, comfortable fit around the patient. The locations of these fasteners can vary and in one embodiment, the pair of fasteners 712, 722 is located below one shoulder strap and the other pair of fasteners 722, 724 is located below the other shoulder strap. In other words, a vertical axis passing through the fastener pair intersects the respective shoulder strap. In another embodiment, the pairs of fasteners are located between the shoulder straps in the fastened position of the garment.

It will be understood that in an alternative embodiment, the first and second sets of fasteners can be the same type of fastener. Alternatively, each set of fasteners can be formed of more than one type of fastener. For example, the second edge (end) can include a strip of hook and loop material and a magnet and similarly, and in a complementary manner, the inner surface (face) of the first wrap section 640 includes a strip of hook and loop material and a magnet.

As discussed herein, magnets possess healing properties and are thought to relieve the feeling of pain and therefore, the magnets can be placed in proximity to the incision and surgical area due to the fact that the magnets are incorporated into the garment design. In addition, the use of two different types of fasteners provides a robust fastening system.

The undergarment 600 also provides the desired functionality to facilitate the recovery phase of the patient. In particular, the undergarment 600 is designed to facilitate the drainage devices that are inserted during the surgery. As described herein, the drainage mechanism 750 can be in the form of a drainage tube 752 which is inserted at one end into the body of the patient and a bulb 754 that is attached to the other end of the drainage tube 752. The undergarment 600 is thus designed to accommodate these components.

In particular, the undergarment 600 includes at least one and preferably one or more pairs of slits 610 formed therein to allow passage of the drainage tubes 752 to the exterior of the garment. The location of the slits 610 is guided by the location of the surgical site and the site of the incision. Thus, the slits 610 are generally in the front of the garment just below the breast area. The slits 610 can be formed at locations that at least partially around a side of the patient. In other words, one end of the slit 610 is located on the front of the garment, while the other end can be located more along the side of the patient. When there are two pairs of slits 610, the slits 610 are spaced apart but can be formed parallel to one another. The slits 610 can also be formed at an angle relative to the bottom edge of the garment. In other words, the slits 610 are not parallel to the bottom edge. The spacing between slits 610 on one side is sufficient to allow passage of the drainage tubes 752 therefrom to the bulbs 754.

The slits 610 can be staggered as shown to assist in routing of the drainage tubes. As shown in FIGS. 6-9, the top slit can be more towards the center of the garment compared to the bottom slit. The degree of overlap, if any, between the pairs of slits 610 can vary. For example, the top slit can at least partially overlap the bottom slit (e.g., up to 50%; or up to 25% overlap) or the top and bottom slits are spaced sufficiently apart and do not overlap at all.

In accordance with the present invention, instead of a slit 610, there can be a series of small holes and the undergarment is formed of an elastic material so as to allow stretch about the hole. Thus, insertion of the tube 752 within the hole will cause the elastic material of the garment to widen, thereby allowing passage of the tube 752. The elastic material of the garment will then hold the tube 752 in place but allow free movement therein.

On the interior (inner face) of the undergarment, there can be a complementary tube retention member 760. The tube retention member 760 can be in the form of an elongated strap that is attached at its ends to the inner face of the undergarment. When the strap 760 is formed of elastic material, it can readily stretch and this characteristic permits the drainage tube to be held in place along the interior of the garment at the desired location. This prevents undesired movement of the drainage tube along the patient's body. The tube retention member 760 is thus located proximate the slit. The tube retention member 760 serves to hold the tube in place. Each slit can have a corresponding tube retention member 760 or there can be a single tube retention member 760 for two or more slits. In this case, two or more drainage tubes are routed through and held in place by the single tube retention member 760.

It will also be appreciated that instead of being permanently fixedly attached at both ends, one end of the elongated strap 760 can be detached from the inner face and attached thereto at a selected location using fasteners. For example, hook and loop material can be placed along the inner face of the garment and also on the free end of the strap. This permits the tube retention member 760 to be easily detached and attached at a desired location for holding the tube retention member 760 in place.

As shown, the exterior surface (face) of the garment that faces outwardly when the garment is worn can also include tube retention members 760 in the form of elastic elongated straps 760.

The undergarment also has a number of other features designed to strategically assist the patient and in particular, the undergarment includes a bulb holder member 770. As shown, the bulb holder 770 can be in the form of an elastic strap that is attached at its ends to the exterior face (surface) of the undergarment. When the strap 770 is formed of elastic material, it can readily stretch and this characteristic permits the drainage tube and/or the bulb to be held in place along the exterior of the undergarment at the desired location. This prevents undesired movement of the drainage tube and/or bulb along the patient's body. The bulb holder is thus located proximate the slit along the exterior surface of the garment. The bulb holder 770 serves to hold the tube and/or bulb in place. Each slit can have a corresponding bulb holder 770 or there can be a single bulb holder 770 for two or more slits. In this case, two or more drainage tubes and bulbs are held in place by the single bulb holder 770.

Figure 6:
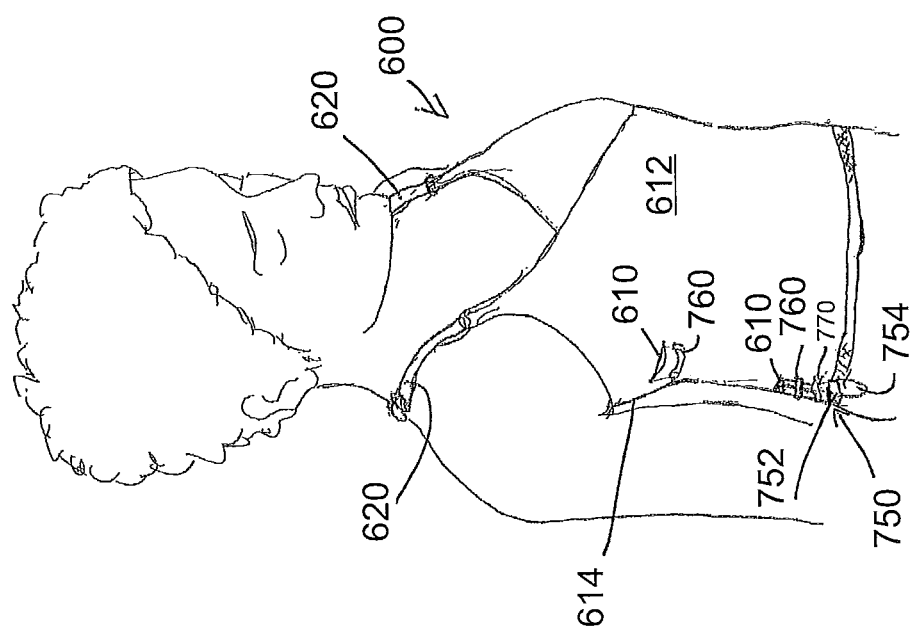
FIG. 6 is a perspective view of a post-surgical brassiere in accordance with another representative embodiment of the present invention.
Figure 7:
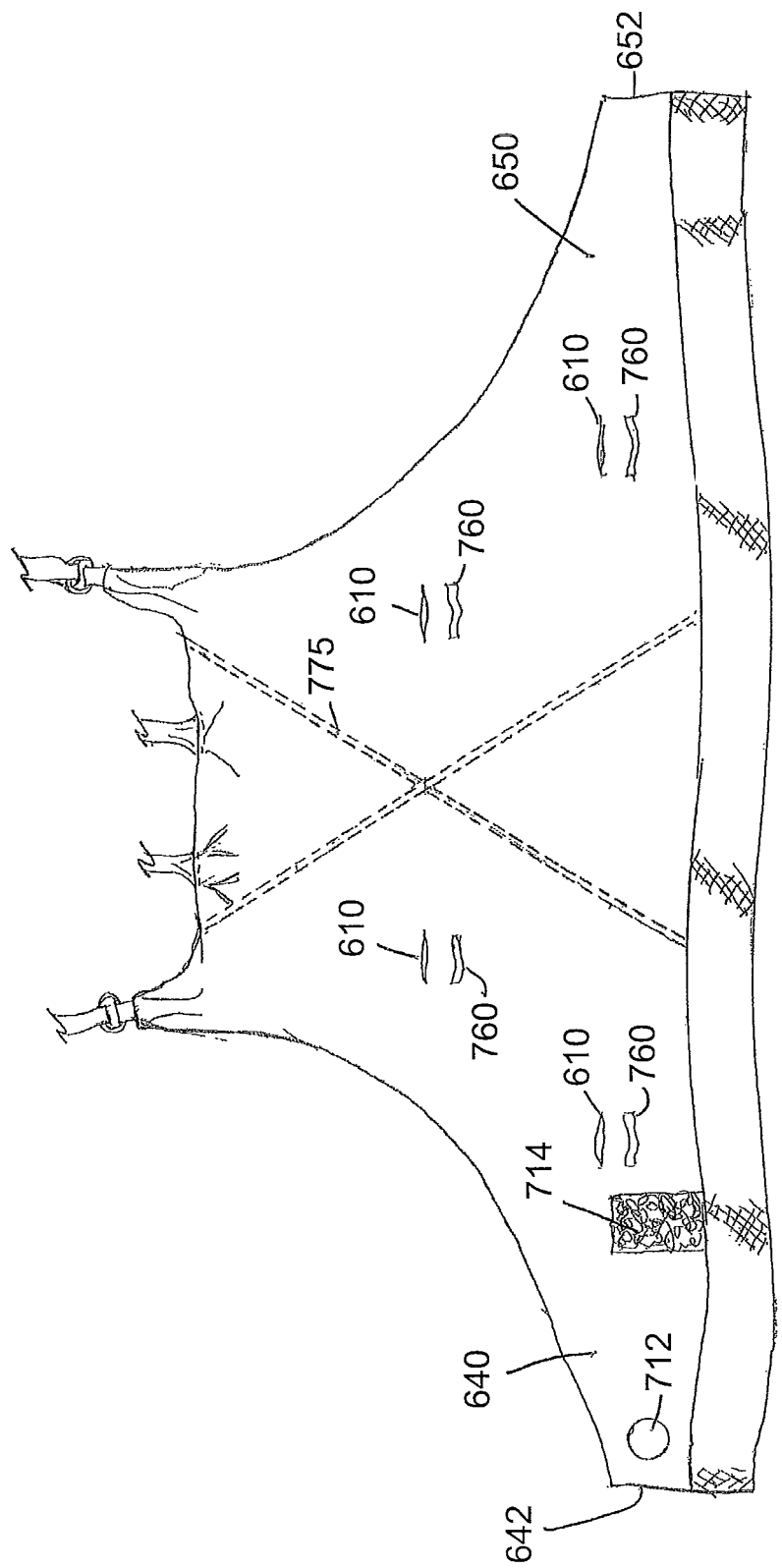
FIG. 7 is a first side elevation view thereof showing the brassiere in an open position.

It will also be appreciated that instead of being permanently fixedly attached at both ends, one end of the bulb holder 770 can be detached from the exterior face and attached thereto at a selected location using fasteners. For example, hook and loop material can be placed along the outer (exterior) face of the garment and also on the free end of the strap. This permits the bulb holder 770 to be easily detached and attached at a desired location for holding the tube retention member 760 in place. The bulb is thus retained along the patient's body. To retain the bulb, the strap is released from the fastener part that is fixed to the outer (exterior) surface and then after insertion of the bulb underneath the strap, the free end of the strap is attached to the respective fastener (hook and loop material), thereby holding the bulb(s) in place. FIG. 6 shows the bulb holder 770 having a diagonal orientation; however, the bulb holder 770 can have a vertical orientation. A horizontal orientation is also equally possible.

Figure 8:
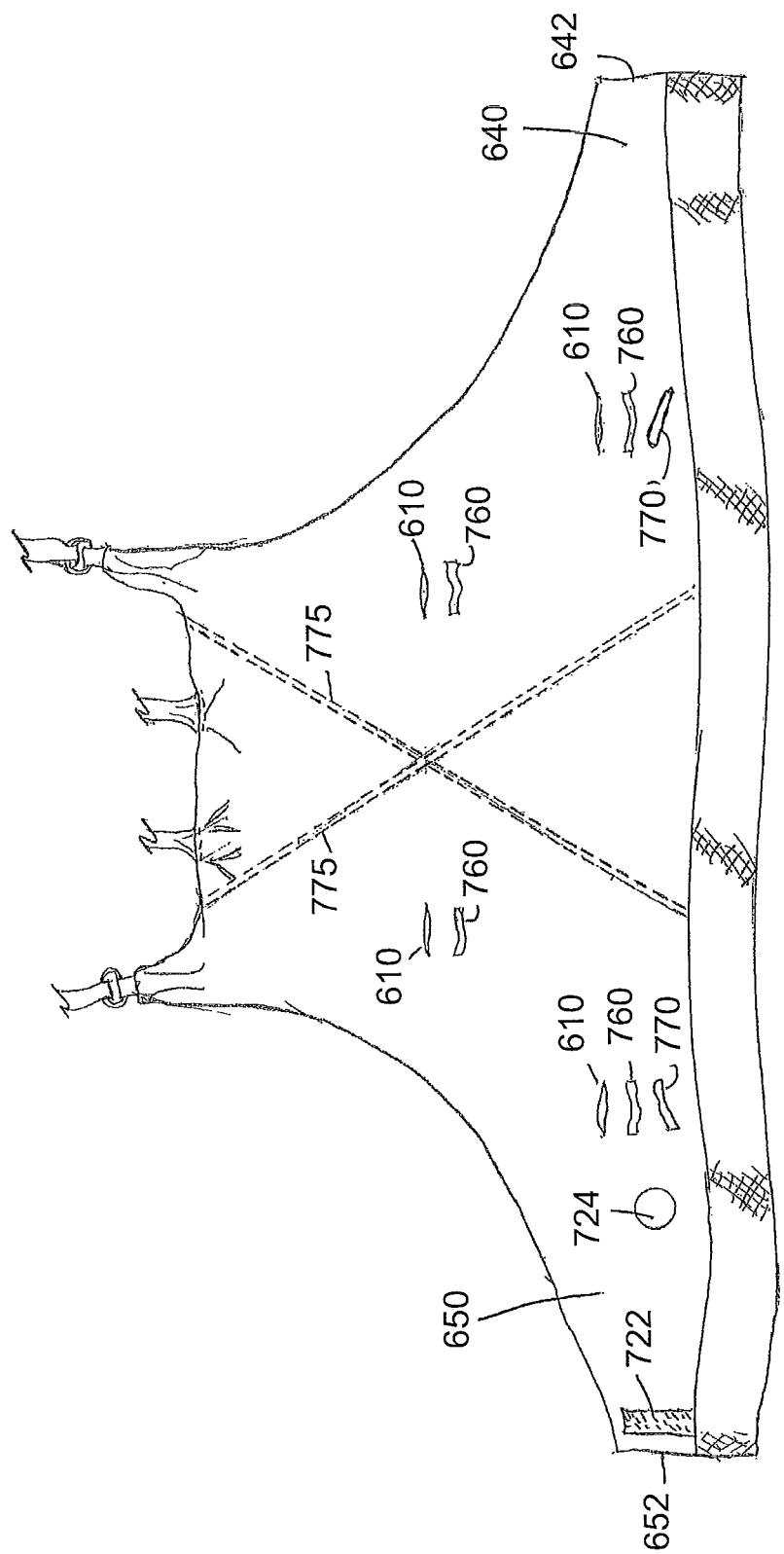
FIG. 8 is an opposite second side elevation view thereof.

As shown in FIG. 8, the rear (back) of the garment can include a CRISSCROSS® member 775 that can be in the form of stitching or elastic material that is securely attached to the rear of the garment using traditional techniques, including stitching, adhesive, or other bonding. The CRISSCROSS® member 775 can provide additional support and compression to the garment as a result of its pattern and/or the material used to form the member 775. The CRISSCROSS® member 775 can be visible on either the front and rear of the garment or visible on both surfaces (faces) as shown depending upon the technique used to form such structure.

In addition, the distance between the pairs of complementary fasteners (e.g., distance between pair 714, 722 and 712, 724) can vary depending upon the construction of the garment. In any event, one fastener pair serves to securely attach the end 752 to the inner surface of wrap portion 740 and the other pair serves to securely attach the end 742 to the exterior surface of the wrap portion 750 so as to optimally provide a secure (e.g., compression) fit around the wearer.

As mentioned herein, the wrap sequence can be reversed and opposite to what is shown in that the second wrap section can be wrapped across and overlie the exterior surface of the first wrap section in which case the magnets and hook and loop material are disposed along the opposite side of the garment relative to what is shown in FIGS. 6-9.

It will also be appreciated that the two attachment points between the two wrap sections 640, 650 can be formed of at least two types of fasteners. For example, the fastener pair defined by members 714, 722 can be formed of two types of fasteners (e.g., a hook and loop patches in combination with mating magnets or hook and loop patches in combination with snaps) and similarly, the fastener pair defined by members 712, 724 can be formed of two types of fasteners (e.g., a hook and loop patches in combination with mating magnets or hook and loop patches in combination with snaps). This type of construction is generally shown in FIG. 10 (discussed below). The fasteners are typically not visible along the front of the assembled garment; however, one or more of the fasteners can be visible along the exterior (front), such as when a magnet is used for fastener 712.

More details and illustration of the bulb holder are described and shown in FIG. 1.

FIG. 10 shows an undergarment 800 according to the present invention. The undergarment 800 is similar to the undergarment 600 in that both include a CRISSCROSS® front construction. The main different between the two undergarments is that the undergarment 800 has a different strap construction. In particular, the shoulder strap construction includes a center ring 810 that is located centrally along the top rear edge of the garment and a pair of shoulder strap routing members 820. The members 820 can be in the form of rings or the like in that the members 820 are fixedly attached to the garment along a top edge of the front thereof and include an opening 822 through which the free ends 832 of a single shoulder strap 830 are passed. The free ends 832 of the strap 830 include a fastener 840, such as a hook and loop material or button, snap, etc., that mates with a complementary to the fastener that is disposed along an inner section of the strap 830. As illustrated, the fasteners 840 can be in the form of a patches, pads, strips, etc., of hook and loop material. The fasteners 840 can be in the form of hook and loop material that allows the shoulder strap(s) to be adjusted by repositioning and attaching the free ends of the strap 830 along the inner sections of the strap 830. As will be appreciated, in this design, a single shoulder strap can be used for both shoulders due to the center ring 810 through which the strap passes from one shoulder area to the other shoulder area.

FIG. 10 shows a series of fasteners that mate with one another similar to the previously described embodiments. In particular, the CRISSCROSS® design is achieved using first and second wrap sections, as in the previous embodiment, that are sequentially wrapped around the patient's body. FIG. 10 shows a similar wrap pattern as FIGS. 6-9 (first wrap section is wrapped across and attached to the exterior face of the second wrap section); however, it will be appreciated that the opposite can be true).

Fasteners 840, 842 and 850, 852 attached the free end of the first wrap section to an exterior surface of the second wrap section spaced from the free edge of the second wrap section. Fastener 870 is part of a fastener system that attaches the free end of the second wrap section to the inner surface of the first wrap section as previously discussed. Fasteners 860, 862 are centrally located along the top edge of the respective wrap sections and serve as a means to centrally attach the two wrap sections to one another.

It will also be understood that the fasteners 860, 862 of FIG. 10 can be incorporated into any of the previous designs including FIGS. 6-9.

As in any of the embodiments described herein, any number of different types of fasteners can be used and the type that is illustrated in a particular location is merely exemplary in nature and not limiting since another type of fastener can easily be substituted therefore.

Now referring to FIGS. 11-12, a garment 900 according to another embodiment is illustrated. The garment 900 incorporated many of the same design features described previously including the CRISSCROSS® front attachment system. However, the garment 900 is intended for a different application in that the garment 900 is intended for medical procedures in which easy access is needed to the chest area (breast area) of the patient. For example, in a medical procedure, such as a radiation treatment or the like, clothing is needed to allow the doctor and/or technician or nurse to easily and selectively expose a target area. In terms of radiation for the breast area, the breast must be accessible to allow radiation or other forms of treatment. At the same, it is desirable to provide an attractive and comfortable garment for the patient.

As with the other garments described previously, the garment 900 includes a center section 915 and two wrap sections 910, 920. Fasteners 940 serve to attach the wrap sections 910, 920 in a CRISSCROSS® manner as disclosed previously. The fasteners 940 can be any number of different types of fasteners including but not limited to snaps, buttons, hook and loop material, magnets, etc.

Unlike the garment in FIGS. 6-9, the garment 900 has shoulder straps 925 that easily detach from the top edge (upper section) of the main body of the garment, thereby allowing one side of the garment to be easily folded down to expose a target area, such as one breast. Each shoulder strap 925 and the top edge of the main body sections include complementary fasteners 930, which once again can be any number of different types of fasteners as disclosed herein. In the illustrated embodiment, the fasteners 930 are in the form of hook and loop material.

One or both of the shoulder straps 925 can be detached from the front of the garment to expose one or more target areas for treatment. Once treatment is complete, the fasteners 930 are attached and the patient is fully covered in an attractive yet versatile garment.

It will be fully understand that the above disclosure and the drawing figures illustrate the incorporation of several of the features of the present invention into various types of garments. However, the invention can be fully implemented in other garment designs and thus, the present garments are exemplary and not limiting.

The CRISSCROSS® construction can thus provide a compression zone or region for wear over the surgical area.

Figure 13:
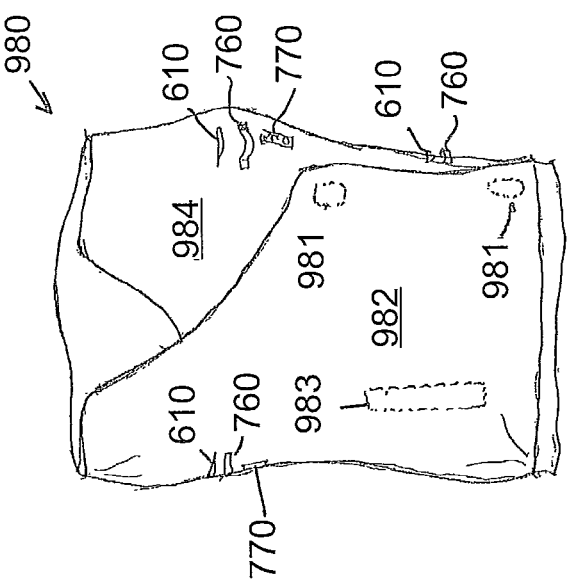
FIG. 13 is a front elevation view of a post-surgical garment according to another embodiment and intended for wear by a male patient.

FIG. 13 shows a garment 980 that is similar to the ones described above with the exception that the garment 980 is intended for use by a male patient. The garment 980, like the other garments, can be a compression type garment that includes a CRISSCROSS® front in that it includes first and second wrap sections 982, 984 that partially overlap and are attached to one another across the front of the patient using a fastening system described herein, such as one or more fasteners of the group consisting of hook and loop material, snaps, buttons, magnets, etc. FIG. 13 shows a pair of magnets 981 mating to one another and a pair of hook and loop patches 983 mating to one another to attach the two wrap sections 982, 984 as described in FIGS. 6-9.

The garment 980 can have shoulders or can be formed to be shoulderless as shown in FIG. 13 (in which case it resembles a tubular garment). The neck can have any number of different designs and there can be shoulders or no shoulders in the design.

Figure 14:
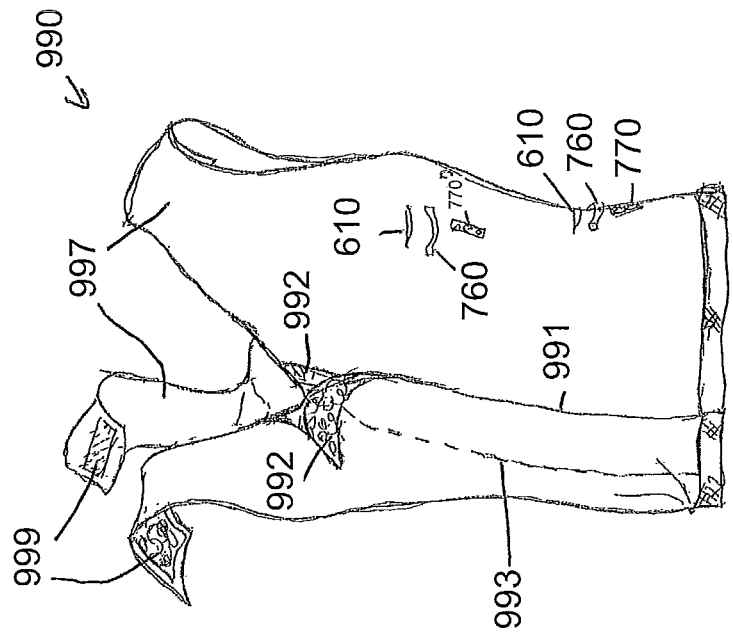
FIG. 14 is a front elevation view of a post-surgical garment according to another embodiment and intended for wear by a male patient.

FIG. 14 shows a garment 990 that is also intended for wear by a male patient. The garment 990 has a center closure 992 that extends vertically and uses any one of the fasteners disclosed herein for securing one side 991 to the other side 993. For example, the closure 992 can be formed of hook and loop material (patches) formed along the edges of the sides 991, 993. Mating the patches 992 (overlapping manner) securely attaches the two sides 991, 993. The garment 990 can include shoulders or can be formed with no shoulders. In addition, the shoulders 997 can be adjustable in that fasteners 999 can be provided at each shoulder 997 to allow the wearer to adjust the fit of the shoulder 997. In the illustrated embodiment, the shoulder 997 is formed of two pieces of fabric with hook and loop material 999 (or other fastener) on each piece to allow the pieces to mate together at a desired location, thereby changing the dimensions and fit of the shoulder 997 (i.e., the shoulder 997 can be made tighter or looser).

In accordance with one aspect of the present invention, the garments disclosed herein can be part of an overall clothing strategy and treatment schedule that is particularly tailored to address the various stages that a breast cancer patient faces. As described throughout the application, it is an objective to provide garments that are not only functional but are also aesthetically pleasing to a patient as they undergo the difficult treatment process. Clothing that is fashionable can boost the morale of the patient.

Figure 15:
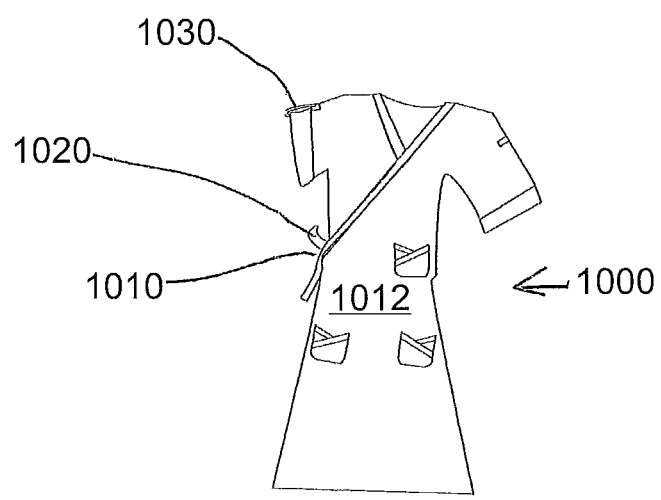
FIG. 15 is a front elevation view of a hospital gown.

The below discussion is merely exemplary of some of the various steps/stages that a cancer patient undergoes and clothing made in accordance with the principles of the present invention is tailored for each step/stage. A first step or stage for many patients is a radiation treatment step and as described herein, the garment shown in FIGS. 11 and 12 is designed to be worn by a patient undergoing such treatment (designed for both men and women). A second step is directed to clothing that is worn post-surgery and in particular, a post-mastectomy surgical bra, such as the ones described herein (e.g., FIGS. 6-9) is worn. In a third step, a post-mastectomy surgical bra with disposable pads is worn by the patient. This garment can be similar to the garment shown in FIGS. 6-9 with the inclusion of disposable pads that are worn by the patient (see FIG. 5). In a fourth step, the patient wears a post-mastectomy surgical camisole that incorporates the features described herein and has a camisole cut. In a fifth step, the patient can wear a post-mastectomy surgical camisole with disposable pads. In a sixth step, a post-mastectomy sports bra can be worn by a patient. The sports bra can incorporate the features of FIGS. 6-9, with a sport bra outline. In a seventh step, a post-mastectomy sports bra or nursing tops can be worn. As the patient recovers and undergoes other activities, garments made in accordance with the present invention can be used. For example, in an eighth step, a post-mastectomy swimsuit or cover-up can be provided for use by a patient. These garments incorporate the features described herein and are formed to have traditional swimsuit and cover-up designs. In a ninth step, a post-mastectomy t-shirt or top can be worn. Once again, these garments are made according to the principles of the present invention and at least have the CRISSCROSS® design that is described herein. In a tenth step, a medical/hospital gown is provided. FIG. 15 shows one exemplary medical gown 1000. The gown 1000 incorporates the CRISSCROSS® side wrap closure 1010 in that a front portion 1012 of the wrap can be wrapped across the front of the person and attached along the side of the person using one of the fastening systems 1020 described herein. For example, the fastening system 1020 can be hook and loop material, a snap, button, magnet, etc. The gown 1000 also includes roll-up sleeves 1030 that are attached with a fastening system, such as hook and loop material, a snap, button, magnet, etc.

Figure 16:
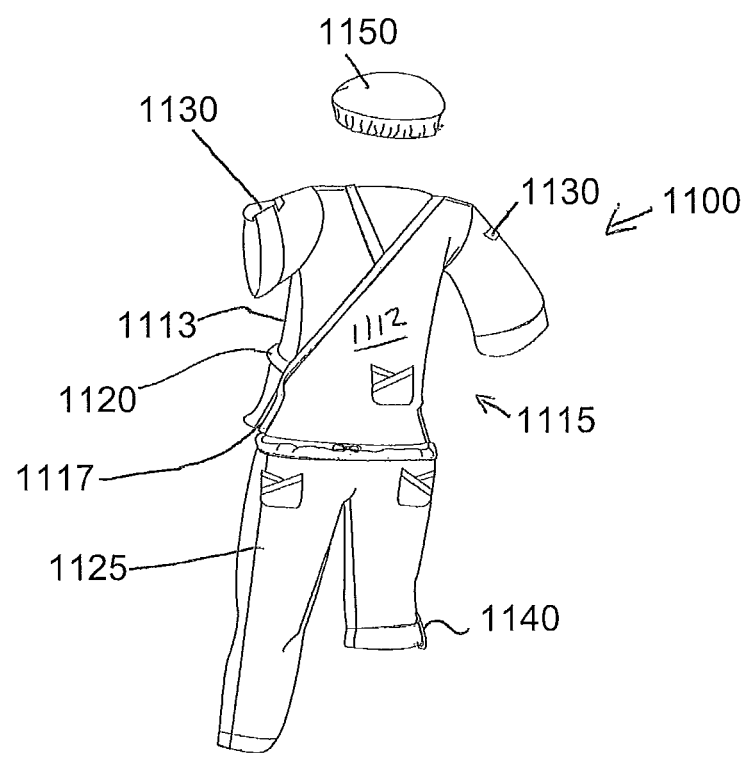
FIG. 16 is a front elevation view of a medical scrub of the present invention.
Figure 17:
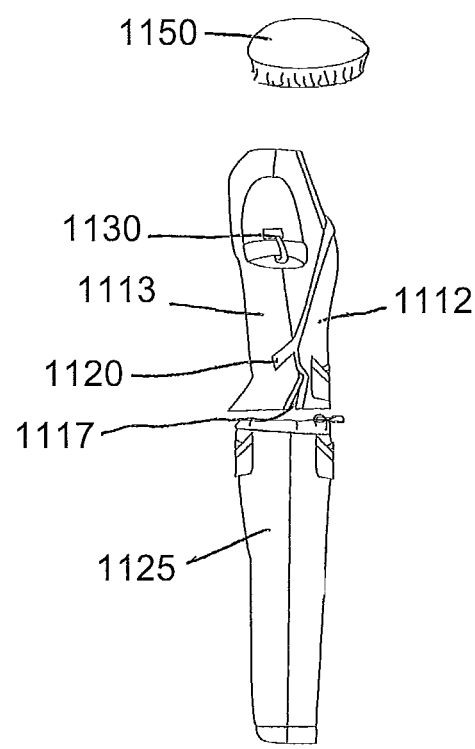
FIG. 17 is a side view thereof.

FIGS. 16-17 illustrate an exemplary medical scrub 1100 in accordance with the present invention and in accordance with the present invention (can be part of an eleventh step). The scrub 1100 incorporates the CRISSCROSS® side wrap closure in that a front portion 1112 of a top 1115 can be wrapped across the front of the person and attached along the side (rear) 1113 of the person using one of the fastening systems 1120 described herein (a slit 1117 is formed between portions 1112 and 1113). For example, the fastening system 1120 can be hook and loop material, a snap, button, magnet, etc. The scrub 1100 also includes roll-up sleeves 1130 that are attached with a fastening system, such as hook and loop material, a snap, button, magnet, etc. The scrub 1100 also includes a bottom 1125 that can have roll-up pant cuffs 1140 that are attached with a fastening system, such as hook and loop material, a snap, button, magnet, etc. A head covering 1150 is provided and can be in the form of a medical scrub cap or turban design that has traditional fitting.

Figure 18:
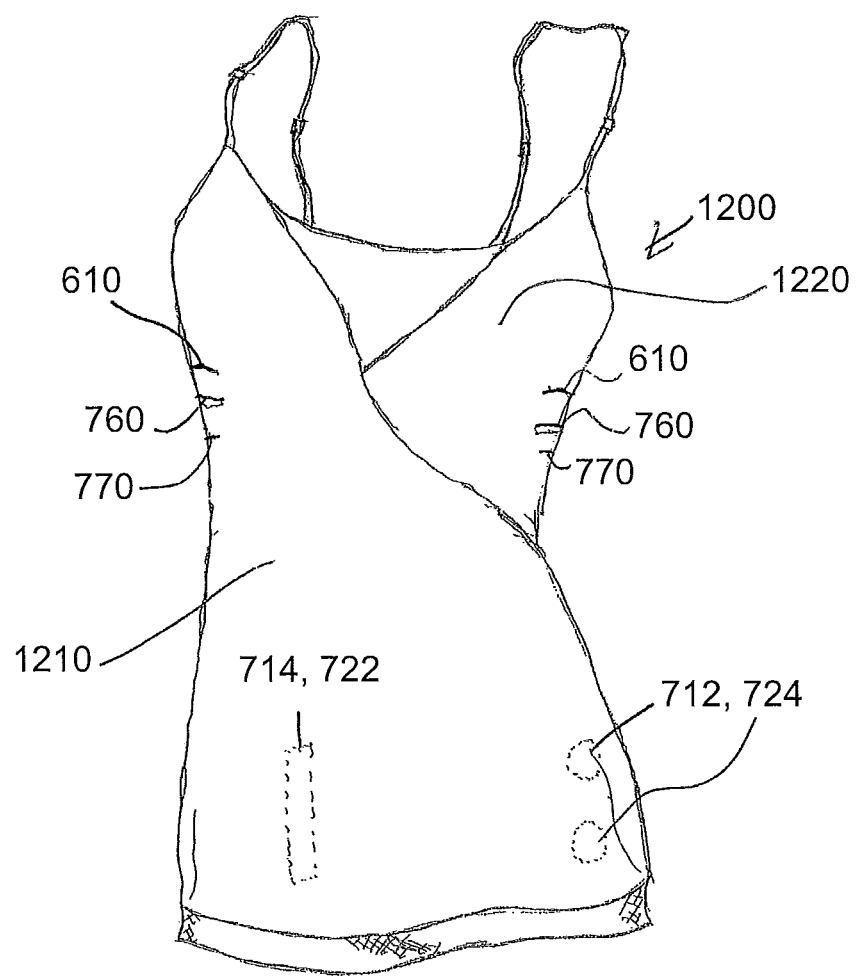
FIG. 18 is a front view of a camisole made in accordance with the present invention.

FIG. 18 shows a camisole 1200 that includes a fitted body formed of suitable material (such as a compression material) and incorporates the CRISSCROSS® construction in that there is a first wrap portion 1210 and a second wrap portion 1220 attached to one other using fasteners as described herein. For example, mating hook and loop patches 714, 722 can be used as well as mating magnets 712, 724; however, as in all of the embodiments disclosed herein, different fasteners can be used to accomplish the attachment between the two wrap portions 1210, 1220 at the indicated areas. Tube holders 760 and bulb holder 770 is also provided as described previously.

Figure 19:
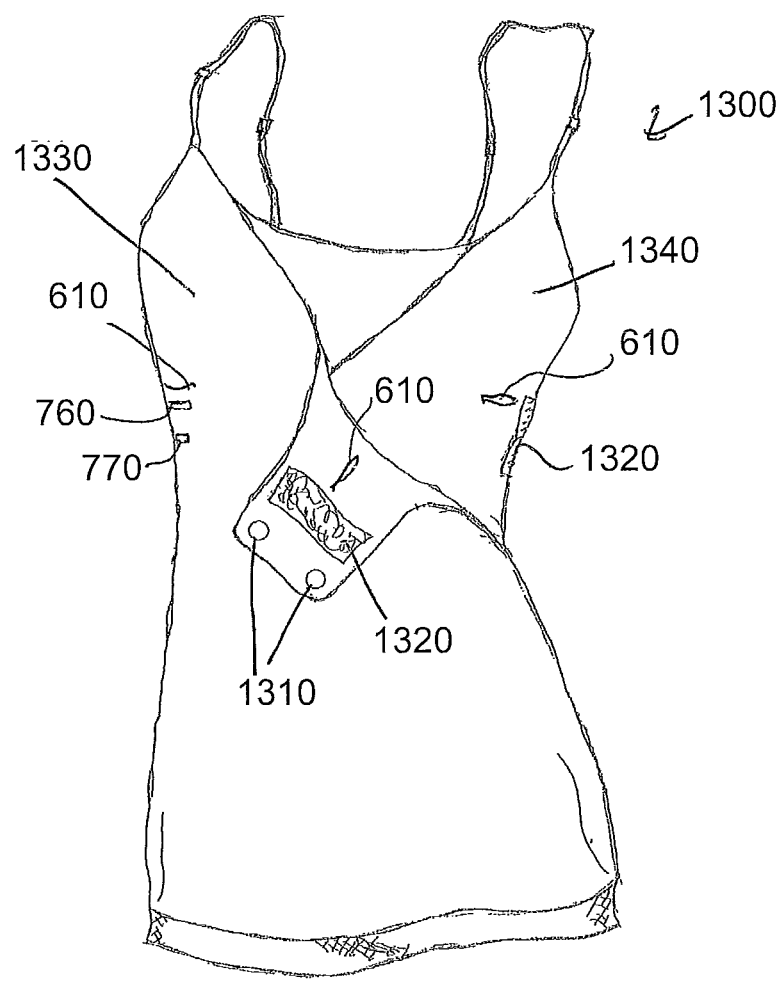
FIG. 19 is a front view of a camisole of alternative design made in accordance with the present invention.

FIG. 19 shows a camisole 1300 that is similar to camisole 1200 with the exception that it includes a fastener system closer to the shoulders. In particular, one or more fasteners, in this case fasteners 1310, 1320 are provided to attach the two wrap portions 1330, 1340. In one embodiment, the fastener 1310 is one or more magnets and the fastener 1320 is a hook and loop material. It will be understood that the camisole 1300 can include the fasteners 712, 714, 722, 724 of FIG. 18 to effectuate a closing of the bottom section of the camisole, while the fasteners 1310, 1320 serve to attach the upper section.

It will also be understood that the camisoles of FIGS. 18 and 19 can be provided without the slits 610 and fasteners 760, 770 depending upon the particular application and the stage of treatment (e.g., whether or not drainage tubes are still being used).

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A post-surgical garment comprising:
   a fabric body having a first end, a second end, a top edge, and a bottom edge;
   a pair of shoulder straps for securing the post-surgical undergarment to the patient and for positioning a compression zone of the fabric body over the surgical site of the patient, wherein a first region of the fabric body is defined between the shoulder straps and is for placement along the back of the patient;
   a first wrap section is defined between one shoulder strap and the first end and a second wrap section is defined between the other shoulder strap and the second end, wherein in an attached position, the first and second wrap sections substantially overlie one another;
   at least one pair of slits formed in the fabric body, one slit being formed proximate the first wrap section, the other slit being formed proximate the second wrap section, the slits being configured to provide access to at least one drainage tube that is inserted into a surgical site of the patient and is configured to mate with a drainage bulb that is disposed along the exterior of the undergarment; and
   a plurality of off-center fasteners to releasably attach the first and second wrap sections to one another, at least one first fastener being disposed along an inner surface of the first wrap section and a second fastener being disposed along an exterior surface of the second wrap section to thereby allow attachment between the inner surface of the first wrap section and the exterior surface of the second wrap section.

2. The post-surgical garment of claim 1, wherein the fabric body is formed of an at least partially elastic material so as to define the compression zone.

3. The post-surgical garment of claim 1, wherein each of the plurality of fasteners is completely contained within the first region.

4. The post-surgical garment of claim 1, wherein there are two pairs of slits defined by a first set that are spaced apart and offset and a second set that are spaced apart and offset.

5. The post-surgical garment of claim 1, further including a set of drainage tube elastic retaining members that are disposed along one of an inner surface and an exterior surface of the fabric body proximate the slits for holding the drainage tubes against the fabric body.

6. The post-surgical garment of claim 5, wherein there are one or more sets of drainage tube elastic retaining members on each of the inner surface and the exterior surface.

7. The post-surgical garment of claim 1, further including a set of elastic bulb retention members, one disposed proximate one slit, the other disposed proximate the other slit, each bulb retention member having a diagonal orientation and being configured to hold the bulb along the exterior of the undergarment.

8. The post-surgical garment of claim 7, wherein elastic bulb retention member is fixedly attached to fabric body at a first end and is releasably attached to the fabric body at an opposite second end.

9. The post-surgical garment of claim 8, the second end including a first fastener that mates with a second fastener attached to the fabric body.

10. The post-surgical garment of claim 1, wherein the plurality of fasteners comprises at least two different types of fasteners, with a first type of fasteners being located at the first end of the first wrap section and an inner section of the second wrap section and a second type of fasteners being located at the second end of the second wrap section and an inner section of the first wrap section.

11. The post-surgical garment of claim 10, wherein the first type of fasteners comprise pieces of hook and loop material and the second type of fasteners comprise magnets.

12. The post-surgical garment of claim 10, wherein the first type of fasteners comprise magnets and the second type of fasteners comprise pieces of hook and loop material.

13. The post-surgical garment of claim 1, wherein the garment is selected from the group consisting of a brassiere; a camisole, a shirt, a gown, and a surgical scrub.

14. A post-surgical garment comprising:
    a fabric body having a first end, a second end, a top edge, and a bottom edge;
    a pair of shoulder straps for securing the post-surgical undergarment to the patient and for positioning a compression zone of the fabric body over the surgical site of the patient;
    a first wrap section defined between one shoulder strap and the first end, and a second wrap section defined between the other shoulder strap and the second end, wherein in an attached position, the first and second wrap sections substantially overlie one another;
    a plurality of slits comprising,
        a first top slit being formed proximate the first wrap section and a second top slit being formed proximate the second wrap section, defining a first pair of slits, and
        a first bottom slit being formed within the first wrap section, and a second bottom slit being formed within the second wrap section, defining a second pair of slits, wherein the first top slit is offset from the first bottom slit and the second top slit is offset from the second bottom slit, the slits being configured to provide access to at least one drainage tube that is inserted into a surgical site of the patient and is configured to mate with a drainage bulb that is disposed along the exterior of the garment; and
    a plurality of off-center fasteners to releasably attach the first and second wrap sections to one another, wherein the plurality of off-center fasteners comprise,
        a first type of fasteners being located at the first end of the first wrap section and an inner section of the second wrap section defining a first pair, and
        a second type of fasteners being located at the second end of the second wrap section and an inner section of the first wrap section, defining a second pair, the plurality of off-center fasteners thereby allowing attachment between the inner surface of the first wrap section and the exterior surface of the second wrap section.

15. The post-surgical garment of claim 14, further including a set of drainage tube elastic retaining members, at least one disposed proximate to the first bottom slit and at least one disposed proximate to the second bottom slit, the drainage tube elastic retaining members being configured to hold the drainage tubes against the fabric body.

16. The post-surgical garment of claim 14, further include a set of elastic bulb retention members, at least one disposed proximate to the first bottom slit and at least one disposed proximate to the second bottom slit, the bulb retention members having a diagonal orientation and configured to hold the bulb along the exterior of the garment.

17. The post-surgical garment of claim 14, wherein the first type of fasteners comprise pieces of hook and loop material and the second type of fasteners comprise magnets.

18. The post-surgical garment of claim 14, wherein the first type of fasteners comprise magnets and the second type of fasteners comprise pieces of hook and loop material.

19. The post-surgical garment of claim 14, wherein the plurality of off-center fasteners further includes a top fastener located along a top portion of the first wrap section and a bottom fastener located along a top portion of the second wrap section, defining a third pair.

20. A post-surgical garment comprising:
a fabric body having a first end, a second end, a top edge, and a bottom edge;
a pair of shoulder strap portions for securing the post-surgical undergarment to the patient and for positioning a compression zone of the fabric body over the surgical site of the patient, wherein a first region of the fabric body is defined between the shoulder strap portions and is for placement along the back of the patient; a first wrap section is defined between one shoulder strap portion and the first end and a second wrap section is defined between the other shoulder strap portion and the second end, wherein in an attached position, the first and second wrap sections substantially overlie one another;
at least one pair of slits formed in the fabric body, one slit being formed proximate the first wrap section, the other slit being formed proximate the second wrap section, the slits being configured to provide access to at least one drainage tube that is inserted into a surgical site of the patient and is configured to mate with a drainage bulb that is disposed along the exterior of the undergarment; and
a plurality of fasteners to releasably attach the first and second wrap sections to one another, at least one first fastener being disposed along an inner surface of the first wrap section and a second fastener being disposed along an exterior surface of the second wrap section to thereby allow attachment between the inner surface of the first wrap section and the exterior surface of the second wrap section, wherein the plurality of fasteners are laterally offset from one another and define and least two different attachment points between the first and second wrap sections, the two different attachment points being laterally offset from one another and spaced inwardly from a free end of the one of the respective first and second wrap sections so as to position the at least two different attachment points at off-center locations with respect to a front of the fabric body when the garment is in the attached position.

21. The post-surgical garment of claim 20, wherein the pair of shoulder strap portions comprise a single elongated strap that is attached at one end to an upper edge of the first wrap section and is attached at an opposite end to an upper edge of the second wrap section, wherein a top edge of the first region of the fabric body includes a routing member through which the single elongated strap passes to allow the single elongated strap to pass from one shoulder area to another shoulder area of the patient.

22. The post-surgical garment of claim 21, wherein the routing member comprises a ring that is attached to the first region of the fabric body.

23. The post-surgical garment of claim 20, wherein the pair of shoulder straps crisscross one another in a region that is for placement along a back of the patient.

* * * * *